United States Patent [19]

Rasberger

[11] 4,386,204
[45] May 31, 1983

[54] 6-PIPERIDINO-DIBENZ[D,G][1,3,6,2]DIOXA-THIOPHOSPHOCINE

[75] Inventor: Michael Rasberger, Riehen, Switzerland

[73] Assignee: Ciba-Geigy Corporation, Ardsley, N.Y.

[21] Appl. No.: 315,123

[22] Filed: Oct. 26, 1981

Related U.S. Application Data

[62] Division of Ser. No. 146,974, May 5, 1980, Pat. No. 4,322,527.

[30] Foreign Application Priority Data

May 15, 1979 [CH] Switzerland ............... 4504/79

[51] Int. Cl.³ ............................................. C07F 9/24
[52] U.S. Cl. ..................................................... 546/21
[58] Field of Search ................... 544/157, 337; 546/21, 546/22; 548/111; 260/923, 927 R, 936, 326.61, 402.5

[56] References Cited

U.S. PATENT DOCUMENTS 3,297,631  1/1967  Bown et al. .................... 524/117
3,993,655  11/1976 Rasberger et al. ............... 546/188
4,055,539  10/1977 Rosenberger .................... 240/333
4,136,041  1/1979  Lenack ............................ 252/46.6

FOREIGN PATENT DOCUMENTS 179918  6/1964  U.S.S.R. .

OTHER PUBLICATIONS

N. A. Mukmeneva et al., CA, 82, 58628v (1975).

Primary Examiner—Robert W. Ramsuer
Attorney, Agent, or Firm—Luther A. R. Hall

[57] ABSTRACT

Compounds of the formula I

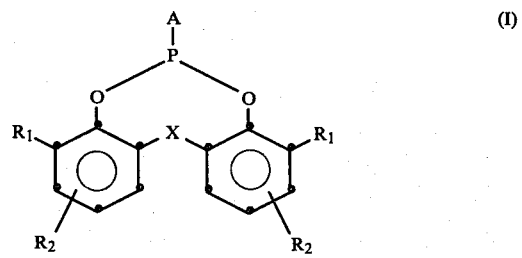

wherein $R_1$ is hydrogen, $C_1$–$C_{18}$ alkyl, $C_5$–$C_{12}$ cycloalkyl, phenyl or $C_7$–$C_9$ phenylalkyl and $R_2$ is hydrogen or $C_1$–$C_{18}$ alkyl, or, if $R_1$ is hydrogen, $R_2$ is a divalent 1,1,3,3-tetramethylpropylene radical fused in the 2-position and 3-position or the 9-position and 10-position, and X is sulfur or a group —CH($R_3$)—, in which $R_3$ is hydrogen or a radical of the formula II —CH($R_4$)—CH($R_5$)S$R_6$, and each of $R_4$ and $R_5$ independently is hydrogen or $C_1$–$C_6$ alkyl and $R_6$ is $C_1$–$C_{20}$ alkyl, while the alkyl group can be interrupted by one or more sulfur atoms, and A is a primary or secondary aliphatic or alicyclic, aromatic or araliphatic amine which contains substituents of the same type or mixed substituents, or a heterocyclic amine or a hydrazine derivative. These compounds are useful stabilizers for organic material.

1 Claim, No Drawings

6-PIPERIDINO-DIBENZ[D,G][1,3,6,2]DIOXATHIO-PHOSPHOCINE

This is a divisional of application Ser. No. 146,974, filed on May 5, 1980, now U.S. Pat. No. 4,322,527, issued on Mar. 30, 1982.

The present invention relates to novel N-substituted 6-amino-dibenz[d,g][1,3,2]dioxaphosphocines, a process for their manufacture, their use as stabilisers for organic material, and the organic material stabilised with these compounds.

Phosphorous acid triesters are known as stabilisers. Thus, for example, substituted 6-phenoxy-12H-dibenz[d,g][1,3,2]dioxaphosphocines are described in U.S. Pat. No. 3,297,631. However, these compounds do not satisfy in every respect the exacting demands which a stabiliser should meet, in particular in respect of storage life, water adsorption, susceptibility to hydrolysis, processing stability, colour properties, volatility, migration properties, compatibility, and improvement in light stabilisation.

It is the object of this invention to provide stabilisers which do not have these disadvantages or which have them to a lesser extent.

Accordingly, the present invention relates to N-substituted 6-amino-dibenz[d,g][1,3,2]dioxaphosphocines of the formula I

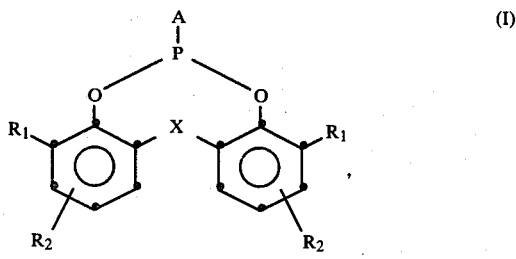

wherein $R_1$ is hydrogen, $C_1$–$C_{18}$ alkyl, $C_5$–$C_{12}$ cycloalkyl, phenyl or $C_7$–$C_9$ phenylalkyl and $R_2$ is hydrogen or $C_1$–$C_{18}$ alkyl, or, if $R_1$ is hydrogen, $R_2$ is a divalent 1,1,3,3-tetramethylpropylene radical fused in the 2- and 3-position or the 9- and 10-position, and X is sulfur or a —CH($R_3$) group, in which $R_3$ is hydrogen or a radical of the formula II —CH($R_4$)—CH($R_5$)S$R_6$, and each of $R_4$ and $R_5$ independently is hydrogen or $C_1$–$C_6$ alkyl and $R_6$ is $C_1$–$C_{20}$ alkyl, while the alkyl group can be interrupted by one or more sulfur atoms, and A is a primary or secondary aliphatic, alicyclic, aromatic or araliphatic amine which contains substituents of the same type or mixed substituents, or a heterocyclic amine or a hydrazine derivative.

$R_1$ and $R_2$ as $C_1$–$C_{18}$ alkyl are in particular straight-chain or branched alkyl of 1 to 8 carbon atoms, for example methyl, ethyl, n-propyl, isopropyl, sec-butyl, tert-butyl, tert-pentyl, n-octyl, 2-ethylhexyl or 1,1,3,3-tetramethylbutyl. $R_1$ is preferably α-branched. In particularly preferred compounds, $R_1$ and $R_2$ are identical and are e.g. tert-butyl.

$R_1$ as $C_5$–$C_{12}$ cycloalkyl can be cyclopentyl, cycloheptyl, cyclooctyl, cyclododecyl and especially cyclohexyl.

$R_1$ as $C_7$–$C_9$ phenylalkyl is e.g. benzyl, 2-phenylethyl or α,α-dimethylbenzyl.

The radicals $R_2$ can be in the 1- and 11-position but are preferably in the 2- and 10-position.

X can be sulfur or a —CHR$_3$ group, in which $R_3$ is preferably hydrogen or a group of the formula II. $R_4$ and $R_5$ as $C_1$–$C_6$ alkyl in formula II are e.g. methyl, ethyl, isopropyl, n-butyl or n-hexyl, but are preferably hydrogen. $R_6$ as $C_1$–$C_{20}$ alkyl is e.g. methyl, ethyl, n-propyl, sec-butyl, n-octyl, n-octadecyl or n-eicosyl and can be interrupted by one or more sulfur atoms. It is preferred, however, that there are at least two carbon atoms between two sulfur atoms. Examples are —(CH$_2$)$_3$—S—(CH$_2$)$_2$—CH$_3$, —CH$_2$CH$_2$—S—(CH$_2$)$_4$—S—CH$_2$CH$_3$ or —CH$_2$CH$_2$—S—CH$_3$. X is preferably —CH$_2$—.

A is a primary or secondary amine which contains substituents of the same type or mixed substituents and which can contain up to six primary and/or secondary amino groups. Preferred compounds are those in which all of the primary or secondary amine nitrogens present in the molecule are substituted by a group of the formula III

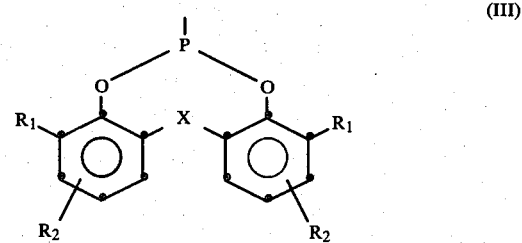

wherein the symbols $R_1$, $R_2$ and X are as defined above.

Especially interesting amines are secondary amines, and in particular branched amines.

Preferred amines A are, therefore, those of the formula IV

wherein $R_7$ is hydrogen, $C_1$–$C_{22}$ alkyl, $C_2$–$C_{21}$ oxa- or thiaalkyl, $C_3$–$C_{18}$ alkenyl, $C_3$–$C_{18}$ alkynyl, $C_2$–$C_6$ hydroxyalkyl, $C_3$–$C_{24}$ alkoxycarbonylalkyl, $C_5$–$C_{12}$ cycloalkyl, $C_6$–$C_{14}$ aryl, $C_7$–$C_{15}$ alkaryl, $C_7$–$C_{15}$ aralkyl, a substituted or unsubstituted $C_5$–$C_{17}$ piperidin-4-yl group or a group of the formula III, in which $R_1$, $R_2$ and X are as defined above, and $R_8$ is $C_1$–$C_{22}$ alkyl, $C_2$–$C_{21}$ oxa- or thiaalkyl, $C_3$–$C_{18}$ alkenyl, $C_3$–$C_{18}$ alkynyl, $C_2$–$C_6$ hydroxyalkyl, $C_3$–$C_{24}$ alkoxycarbonylalkyl, $C_5$–$C_{12}$ cycloalkyl, $C_6$–$C_{14}$ aryl, $C_7$–$C_{15}$ alkaryl, $C_7$–$C_{15}$ aralkyl, a substituted or unsubstituted $C_5$–$C_{17}$ piperidin-4- or -1-yl group or a group of the formula

or

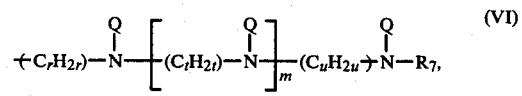

wherein $R_7$ is as defined above and n is 0 or 1 and $R_9$ is $C_2$–$C_{22}$ alkylene which can be interrupted by one or two oxygen or sulfur atoms, or is $C_4$–$C_{22}$ alkenylene, $C_4$-$C_{22}$ alkynylene, $C_5$-$C_9$ cycloalkylene or a group of the formula VII

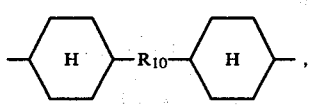

in which $R_{10}$ is —O—, —S— or —($R_{11}$)C($R_{12}$)—, in which each of $R_{11}$ and $R_{12}$ independently is hydrogen or $C_1$-$C_8$ alkyl, or $R_{11}$ and $R_{12}$ together with the carbon atom to which they are attached form $C_5$-$C_{12}$ cycloalkyl; and $R_9$ is also phenylene, biphenylene or a group of the formula VIII

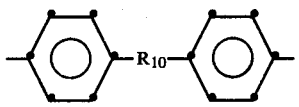

in which $R_{10}$ is as defined above, and each of r, t and u independently is 2, 3, 4, 5 or 6 and m is 0, 1, 2 or 3, and Q is a group of the formula III, in which $R_1$, $R_2$ and X are as defined above; or $R_7$ and $R_8$ together with the nitrogen atom to which they are attached are substituted pyrrolidine, oxazolidine, piperidine or morpholine, or $R_7$ and $R_8$ together form the radical —CH$_2$—CH$_2$—N(Q)—CH$_2$—CH$_2$—, in which Q is as defined above.

$R_7$ and $R_8$ as $C_1$-$C_{22}$ alkyl can be methyl, ethyl, n-propyl, isopropyl, n-butyl, sec-butyl, tert-butyl, n-pentyl, n-hexyl, isohexyl, n-octyl, 1,1,3,3-tetramethylbutyl, n-nonyl, decyl, dodecyl, tetradecyl, hexadecyl, octadecyl, eicosyl or docosyl. Alkyl groups $R_7$ and $R_8$ preferably contain 1 to 18 carbon atoms. In particular, $R_7$ and $R_8$ contain 1 to 12 and 1 to 4 carbon atoms respectively. $R_7$ and $R_8$ as oxa- and thiaalkyl of 2 to 21, especially 4 to 21, carbon atoms, are preferably alkoxy- or alkylthiopropyl, such as butoxypropyl, dodecylthiopropyl, octyloxypropyl or octadecyloxypropyl.

$R_7$ and $R_8$ as $C_3$-$C_{18}$ alkenyl are e.g. allyl, methallyl, n-hex-3-enyl, n-oct-4-enyl or n-undec-10-enyl. Preferred radicals are allyl and methallyl, and especially allyl.

$R_7$ and $R_8$ as $C_3$-$C_{18}$ alkynyl are e.g. propargyl, n-but-1-ynyl, n-but-2-ynyl or n-hex-1-ynyl. Preferred alkynyl groups are those containing 3 or 4 carbon atoms and especially propargyl.

$R_7$ and $R_8$ as hydroxyalkyl containing 1 to 6 carbon atoms can be 2-hydroxypropyl, 2-hydroxyethyl, 3-hydroxypropyl, 4-hydroxybutyl or 6-hydroxyhexyl.

$R_7$ and $R_8$ as $C_3$-$C_{24}$ alkoxycarbonylalkyl, preferably $C_3$-$C_{24}$ alkoxycarbonylmethyl or -ethyl, and in particular $C_3$-$C_{14}$ alkoxycarbonylmethyl or $C_3$-$C_{15}$ alkoxycarbonylethyl, can be e.g. methoxycarbonylmethyl, ethoxycarbonylmethyl, methoxycarbonylethyl, octoxycarbonylmethyl, octoxycarbonylbutyl, dodecyloxycarbonylethyl or octadecyloxycarbonylethyl.

$R_7$ and $R_8$ as cycloalkyl of 5 to 12, preferably 5 to 8 and most preferably 6, carbon atoms, are e.g. cyclopentyl, cyclohexyl, cycloheptyl, cyclooctyl, cyclononyl or cyclododecyl.

$R_7$ and $R_8$ as $C_6$-$C_{14}$ aryl are e.g. phenyl, α-naphthyl, β-naphthyl or phenanthryl. Phenyl groups are preferred.

$R_7$ and $R_8$ as aralkyl containing 7 to 15 carbon atoms are e.g. benzyl, α-phenylethyl, α,α-dimethylbenzyl or 2-phenylethyl, preferably benzyl.

$R_7$ and $R_8$ as $C_7$-$C_{15}$ alkaryl groups can be e.g. tolyl, 2,6-dimethylphenyl, 2,6-diethylphenyl, 2,4,6-triisopropylphenyl or 4-tert-butylphenyl.

If $R_7$ is a group of the formula III, this group is preferably substituted in the same way as the dibenz[d,g][1,3,2]dioxaphosphocin-6-yl radical already present in the molecule.

If $R_7$ and $R_8$ together with the nitrogen atom to which they are attached form a pyrrolidine, oxazolidine or morpholine ring, these heterocyclic rings can be substituted by up to five methyl or ethyl groups. These ring systems are preferably unsubstituted.

$R_7$ and $R_8$ as $C_5$-$C_{17}$ piperidin-4-yl groups can be e.g. unsubstituted piperidin-4-yl, or the piperidine can be substituted by up to 5 alkyl groups, preferably by methyl or ethyl groups. Preferred positions for substitution are the 2-position and the 6-position in the piperidine ring. The groups can also be 3,3,5-trimethyl-8-ethoxy-bicyclo[4.4.0]dec-2-yl.

$R_7$ and $R_8$ can therefore form piperidin-4-yl or piperidin-1-yl groups of the following constitution:

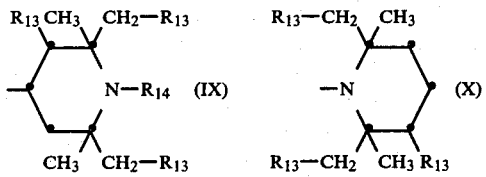

in which $R_{13}$ is hydrogen or methyl and $R_{14}$ is hydrogen, oxyl, $C_1$-$C_{18}$ alkyl, $C_3$-$C_8$ alkenyl, $C_3$-$C_6$ alkynyl, $C_7$-$C_{12}$ aralkyl, $C_2$-$C_{21}$ alkoxyalkyl, an aliphatic acyl group containing 1 to 4 carbon atoms or a —CH$_2$COOR$_{15}$ group, in which $R_{15}$ is $C_1$-$C_{12}$ alkyl, $C_3$-$C_8$ alkenyl, phenyl, $C_7$-$C_8$ aralkyl or cyclohexyl.

The most preferred piperidin-4-yl radicals are those in which $R_{13}$ is hydrogen and $R_{14}$ is hydrogen, methyl or acetyl. $R_{13}$ is preferably hydrogen.

$R_{14}$ as $C_1$-$C_{18}$ alkyl is e.g. methyl, ethyl, n-propyl, n-butyl, n-pentyl, n-octyl, n-decyl, n-dodecyl or octadecyl. Preferred alkyl groups are those containing 1 to 12 carbon atoms, and also those containing 1 to 8 carbon atoms, and especially those containing 1 to 4 carbon atoms, in particular methyl.

$R_{14}$ as $C_3$-$C_8$ alkenyl is e.g. allyl, 3-methyl-2-butenyl, 2-butenyl, 2-hexenyl or 2-octenyl, especially allyl.

$R_{14}$ as $C_3$-$C_6$ alkynyl is e.g. propargyl.

$R_{14}$ as $C_7$-$C_{12}$ aralkyl is e.g. benzyl, β-phenylethyl or 4-tert-butylbenzyl, preferably benzyl.

Where $R_{14}$ is $C_2$-$C_{21}$ alkoxyalkyl, the alkyl moiety can contain 1 to 3 carbon atoms and the alkoxy moiety can contain 1 to 18 carbon atoms, for example methoxymethyl, ethoxymethyl, 2-methoxyethyl, 2-ethoxyethyl, 2-n-butoxyethyl, 3-n-butoxypropyl, 2-octoxyethyl or 2-octadecyloxyethyl. Preferred compounds are those in which $R_{14}$ is an alkoxyalkyl group containing 2 to 6 carbon atoms.

As an aliphatic acyl group having 1 to 4 carbon atoms, $R_{14}$ is e.g. formyl, acetyl, acryloyl or crotonyl, especially acetyl.

If $R_{14}$ is the —CH$_2$COOR$_{15}$ group, $R_{15}$ as $C_1$-$C_{12}$ alkyl is e.g. methyl, ethyl, isopropyl, n-butyl, isobutyl, tert-butyl, isopentyl, n-octyl or n-dodecyl. $R_{15}$ is preferably $C_1$–$C_4$ alkyl. $R_{15}$ as $C_3$–$C_8$ alkenyl is e.g. allyl, 2-butenyl or 2-hexenyl. $R_{15}$ as $C_7$–$C_8$ aralkyl is e.g. benzyl or α-phenylethyl.

n can be 0 or preferably 1.

$R_9$ as $C_2$–$C_{22}$ alkylene, preferably $C_2$–$C_9$ alkylene and in particular $C_2$–$C_6$ alkylene, can be e.g. dimethylene, trimethylene, tetramethylene, hexamethylene, octamethylene, nonamethylene, 2,2,4-trimethylhexamethylene, decamethylene, dodecamethylene, octadecamethylene or docosamethylene. If the alkylene groups are interrupted by —O— or —S—, these groups can be 2-thia-1,3-propylene, 3-thia-1,5-pentylene, 4-oxaheptamethylene or 3,6-dioxa-1,8-octylene.

$R_9$ as $C_4$–$C_{22}$ alkylene or alkynylene is e.g. 2-butenylene-1,4; 2-butylene-1,4; 2,4-hexadiynylene-1,6 or propenylene-1,3.

$R_9$ as $C_5$–$C_9$ cycloalkylene is e.g. 1,2-cyclopentylene, 1,2-cyclohexylene, 1,3-cyclohexylene, 1,4-cyclohexylene, 1,4-cycloheptylene or 1,2-cyclononylene. As cycloalkylene $R_9$ preferably contains 6 carbon atoms.

$R_{11}$ and $R_{12}$ as $C_1$–$C_8$ alkyl are e.g. ethyl, n-propyl, isopropyl, n-butyl, n-phenyl, n-hexyl or n-octyl; it is preferred, however, that alkyl groups $R_{11}$ and $R_{12}$ are methyl.

$R_{11}$ and $R_{12}$ together with the carbon atom to which they are attached can also form $C_5$–$C_{12}$ cycloalkyl, preferably cyclohexyl. The cycloalkyl group can be cyclopentyl, cyclohexyl, cycloheptyl, cyclooctyl or cyclododecyl.

Each of r, t and u independently is 2, 3, 4, 5 or 6, but is preferably the same and most preferably is 2 or 3.

m can be 0, 1, 2 or 3. Preferably m is 0 or 1 and is most preferably 0.

If the compounds contain radicals Q, the latter preferably have the same substituents as the other dibenz[d,g][1,3,2]dioxaphosphocin-6-yl radicals present in the molecule.

Preferred compounds of the formula I are those in which $R_1$ and $R_2$ are $C_1$–$C_{18}$ alkyl, and $R_2$ is also hydrogen, and X is sulfur or —CH$_2$— and A is a group —N($R_7$)$R_8$, in which $R_7$ is hydrogen, $C_1$–$C_{18}$ alkyl, $C_3$–$C_4$ alkenyl, $C_3$–$C_4$ alkynyl, $C_3$–$C_{24}$ alkoxycarbonylmethyl or -ethyl, $C_5$–$C_{12}$ cycloalkyl, phenyl, benzyl, $C_7$–$C_{15}$ alkaryl, a substituted or unsubstituted $C_5$–$C_{17}$ piperidin-4-yl group or a group of the formula III, in which $R_1$, $R_2$ and X are as defined above, and $R_8$ is $C_1$–$C_{18}$ alkyl, $C_3$–$C_4$ alkenyl, $C_3$–$C_4$ alkynyl, $C_3$–$C_{24}$ alkoxycarbonylmethyl or -ethyl, $C_5$–$C_{12}$ cycloalkyl, phenyl, benzyl, $C_7$–$C_{15}$ alkaryl, a substituted or unsubstituted $C_5$–$C_{17}$ piperidin-4-yl group or a group of the formula V or VI, in which $R_7$ is as defined above and n is 0 or 1 and $R_9$ is $C_2$–$C_9$ alkylene which can be interrupted by one or two oxygen or sulfur atoms, or is cyclohexylene or a group of the formula VII, in which $R_{10}$ is —O—, —S— or —($R_{11}$)C($R_{12}$)—, in which each of $R_{11}$ and $R_{12}$ independently is hydrogen or methyl, or $R_{11}$ and $R_{12}$ together with the carbon atom to which they are attached form cyclohexylene, and r, t and u are 2 or 3 and m is 0 or 1 and Q is a group of the formula III, in which $R_1$, $R_2$ and X are as defined above, or $R_7$ and $R_8$ together with the nitrogen atom to which they are attached form a pyrrolidine, oxazolidine, piperidine or morpholine ring, or $R_7$ and $R_8$ together are the radical —CH$_2$CH$_2$—N(Q)—CH$_2$CH$_2$—, in which Q is as defined above.

Interesting compounds of the formula I are those in which $R_1$ is α-branched $C_3$–$C_8$ alkyl and $R_2$ is $C_1$–$C_8$ alkyl and X is sulfur or —CH$_2$— and A is a group —N($R_7$)$R_8$ (IV), in which $R_7$ is hydrogen, $C_1$–$C_{18}$ alkyl, allyl, propargyl, $C_3$–$C_{14}$ alkoxycarbonylmethyl, $C_3$–$C_{15}$ alkoxycarbonylethyl or $C_5$–$C_8$ cycloalkyl and $R_8$ is $C_1$–$C_4$ alkyl, allyl, propargyl, $C_3$–$C_{14}$ alkoxycarbonylmethyl, $C_3$–$C_{15}$ alkoxycarbonylmethyl, $C_5$–$C_8$ cycloalkyl or a group of the formula V or VI, in which $R_7$ is as defined above and n is 1 and $R_9$ is $C_2$–$C_6$ alkylene and r, t and u are 2 or 3 and m is 0 and Q is a group of the formula III, in which $R_1$, $R_2$ and X are as defined above, or $R_7$ and $R_8$ together with the carbon atom to which they are attached form a piperidine or morpholine ring, or $R_7$ and $R_8$ together are the radical —CH$_2$CH$_2$—N(Q)—CH$_2$CH$_2$—, in which Q is as defined above.

Particularly preferred compounds of the formula I are those in which $R_1$ and $R_2$ are α-branched $C_3$–$C_8$ alkyl and X is sulfur or —CH$_2$— and A is a group —N($R_7$)$R_8$ (IV), in which $R_7$ is hydrogen, $C_1$–$C_{12}$ alkyl or cyclohexyl and $R_8$ is $C_1$–$C_4$ alkyl, cyclohexyl or a group of the formula V, in which $R_7$ is as defined above and Q is a group of the formula III, in which $R_1$, $R_2$ and X are as defined above, and n is 1 and $R_9$ is $C_2$–$C_6$ alkylene, or $R_7$ and $R_8$ together with the carbon atom to which they are attached form a piperidine or morpholine ring, or $R_7$ and $R_8$ together are the radical —CH$_2$CH$_2$—N(Q)—CH$_2$CH$_2$—, in which Q is as defined above.

Examples of compounds of the formula I are:

(1) 6-(di-n-octylamino)-2,4,8,10-tetra-tert-butyl-12H-dibenz[d,g][1,3,2]dioxaphosphocine, (2) 6-(2'-aza-3',3',5'-trimethyl-8'-ethoxy-bicyclo[4.4.0]dec-2'-yl)-2,4,8,10-tetra-tert-butyl-dibenz[d,g][1,3,6,2]dioxa-thiaphosphocine, (3) 6-(N-2',6'-dimethylphenyl-N-cyclohexylamino)-2,10-dimethyl-4,8-di-tert-butyl-dibenz[d,g][1,3,6,2-]dioxathiaphosphocine, (4) 6-(dicyclohexylamino)-2,4,8,10-tetra-tertbutyl-12H-dibenz[d,g][1,3,2]dioxaphosphocine, (5) 6-(N,N-dimethylamino)-2,4,8,10-tetra-(1',1',3',3'-tetramethylbutyl)-dibenz[d,g][1,3,6,2]dioxa-thia-phosphocine, (6) 6-morpholino-2,4,8,10-tetramethyl-12H-dibenz[d,g][1,3,2]dioxa-phosphocine, (7) 6-(di-n-butylamino)-2,10-dimethyl-4,8-di-tertbutyl-12-(2'-dodecylthio-propyl)-12H-dibenz[d,g][1,3,2]dioxaphosphocine, (8) 6-[di-(hydroxyethyl)-amino]2,10-di-(1',1',3',3'-tetramethylbutyl)-dibenz[d,g][1,3,6]dioxathiaphosphocine, (9) 6-(2',4'-dimethylanilino)-2,4,8,10-tetra-tertbutyl-dibenz[d,g][1,3,6,2]dioxa-thiaphosphocine,

(10) 6-[p-(phenylamino)-anilino]-2,10-dimethyl-4,8-di-tert-butyl-12H-dibenz[d,g][1,3,2]dioxaphosphocine,

(11) (Z—CH$_2$CH$_2$O)$_2$N—Z (*)

(12) (CH$_3$CH$_2$—N(Z)—CH$_2$CH$_2$)$_2$—N—Z (*)

(13) CH$_3$—(CH$_2$)$_3$—CH(C$_2$H$_5$)—CH$_2$—N—(Z)$_2$ (*)

(14)

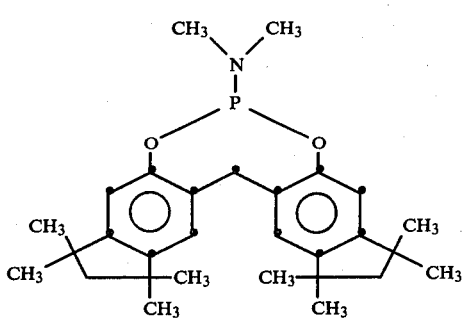

(*) In the formulae 11 to 13 above, Z is a group of the formula III, in which $R_1$ and $R_2$ are tert-butyl and X is —$CH_2$—.

Compound 14 exemplifies a compound in which $R_2$ forms a 1,1,3,3-tetramethylpropylene radical fused in the 2- and 3-position or 10- and 11-position.

The phosphites of the formula I can be obtained by methods known per se, especially by amidation or transamidation processes, for example by reacting a phosphorous acid diester of the formula X

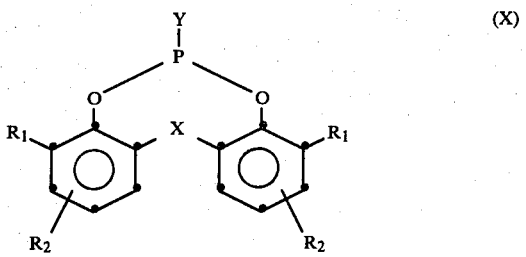

in which Y is a reactive group and $R_1$, $R_2$ and X are as defined above, with an amine $R_{16}$-A, in particular with an amine of the formula $$R_{16}N(R_7)R_8 \qquad (XI)$$

in which $R_{16}$ is hydrogen or a Na, Li or K atom and A, $R_7$ and $R_8$ are as defined above.

A reactive group Y is e.g. halogen, especially chlorine, or alkoxy, phenoxy, or a primary or secondary amino group.

An alternative method of obtaining compounds of the formula I comprises reacting a phosphorus amide of the formula $$(Hal)_2-P-A \qquad (XII)$$

in which Hal is a halogen atom, especially chlorine, and Z is as defined above, with a diphenol of the formula

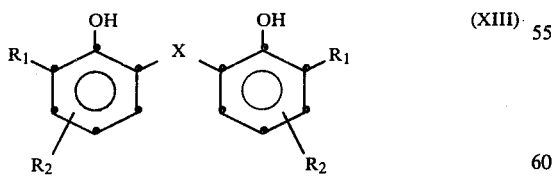

in which $R_1$, $R_2$ and X are as defined above.

Both types of reaction can be carried out in a manner known per se, for example in the temperature range from −5° C. to 80° C., or by heating, preferably to a temperature above about 80° C., for example in the range from 80°–170° C. The reaction can be carried out without a solvent or in the presence of an inert solvent, such as an aprotic solvent, for example ligroin, toluene, xylene, hexane, cyclohexane, dimethylformamide, dimethylacetamide, sulfolane, acetonitrile, dioxane, di-n-butyl ether 1,2-dichloroethane, dimethyl sulfoxide, ethyl acetate, methyl ethyl ketone, nitrobenzene, nitromethane, tetrahydrofurane chloroform or trichloroethylene. If X is halogen, the reaction is advantageously carried out in the presence of a base, such as sodium carbonate or an amine, for example triethylamine, pyridine or N,N-dimethylaniline. However, it is entirely possible to carry out the reaction with an excess of the amine of the formula XI, in which case this amine acts as acid acceptor. Amine bases employed in excess can at the same time act as solvents.

The starting materials of the formulae X, XI, XII and XIII are known, or, if they are novel, can be prepared analogously to known compounds. The phosphites of the formula X can be prepared from the corresponding diphenol compounds of the formula XIII and $PY_3$, in which Y is as defined above. Diphenol compounds of the formula XIII in which —X— is a —$CH_2$— group can be prepared by methods analogous to those described in U.S. Pat. No. 4,055,539.

In the practice of the present invention, the compounds of the formula I can be used as stabilisers for protecting plastics and elastomers against damage caused by the action of oxygen, light and heat. Examples of such plastics are the polymers listed on pages 12–14 of German Offenlegungsschrift 2 456 864.

Examples of suitable substrates are:
1. Polymers which are derived from monounsaturated hydrocarbons, such as polyolefins, for example low density and high density polyethylene which may or may not be crosslinked, polypropylene, polyisobutylene, polymethylbut-1-ene and polymethylpent-1-ene.
2. Mixtures of the homopolymers listed under 1, for example mixtures of polypropylene and polyethylene, of polypropylene and polybut-1-ene and of polypropylene and polyisobutylene.
3. Copolymers of the monomers on which the homopolymers listed under 1 are based, such as ethylene/propylene copolymers, propylene/but-1-ene copolymers, propylene/isobutylene copolymers and ethylene/but-1-ene copolymers, and also terpolymers of ethylene and propylene with a diene, for example hexadiene, dicyclopentadiene or ethylidenenorbornene.
4. Polystyrene and its copolymers, such as SAN, ABS, IPS, ASA and EP modified styrene copolymers.
5. Polyamides.
6. Linear polyesters.
7. Polyurethanes.
8. Polycarbonates.
9. Elastomers, such as polybutadiene, SBR, polyisoprene, polychloroprene and nitrile rubber.
10. Thermoplastic elastomers, such as SBS, SIS and S-EP-S.
11. Polyvinyl chloride and the like.
12. Synthetic- and mineral-based lubricating oils.

The present invention also relates to a method of stabilising polymers against degradation caused by heat and oxidation during production, isolation, processing and use, which method comprises incorporating at least one compound of the formula I in the polymer.

The compounds of the formula I are incorporated in the substrates in a concentration of 0.005 to 5% by weight, based on the material to be stabilised.

Preferably, 0.01 to 1.0, and most preferably 0.02 to 0.5%, by weight of the compounds, based on the material to be stabilised, is incorporated into the latter. Incorporation can be effected, for example, by blending in at least one of the compounds of the formula I and, if desired, further additives, by the methods conventionally employed in the art, before or during shaping, or by applying the dissolved or dispersed compounds to the polymer, with subsequent evaporation of the solvent if desired.

The novel compounds can also be added to the plastics to be stabilised in the form of a master batch which contains these compounds, for example in a concentration of 2.5 to 25% by weight.

In the case of crosslinked polyethylene, the compounds are added before crosslinking.

The invention therefore also relates to the plastics which are stabilised by the addition of 0.01 to 5% by weight of a compound of the formula I and which, if desired, can also contain further additives. The plastics stabilised in this way can be employed in very diverse forms, for example in the form of films, fibres, ribbons or profiles or as binders for lacquers, adhesives or putties.

Examples of further additives together with which the stabilisers can be employed are: antioxidants, UV absorbers and light stabilisers, such as 2-(2'-hydroxyphenyl)-benztriazoles, 2,4-bis-(2'-hydroxyphenyl)-6-alkyl-s-triazines, 2-hydroxybenzophenones, 1,3-bis-(2'-hydroxybenzoyl)-benzenes, esters of substituted or unsubstituted benzoic acids and acrylates, and furthermore nickel compounds, sterically hindered amines, oxalic acid diamides, metal deactivators, phosphites, compounds which destroy peroxide, polyamide stabilisers, basic costabilisers, nucleating agents or other additives, for example plasticisers, lubricants, emulsifiers, fillers, carbon black, asbestos, kaolin, talc, glass fibres, pigments, fluorescent whitening agents, flame retardants and antistatic agents.

The following examples illustrate the invention in more detail.

EXAMPLE 17.9 g of 2,2'-thio-bis-(4-methyl-6-tertbutyl)-phenol, 5 ml of phosphorus trichloride and 30 ml of xylene are heated slowly to 90°-100° C. After a reaction time of five hours, the mixture is cooled to room temperature. Then 5.5 g of triethylamine and 4.5 g of piperidine are added and the mixture is kept at reflux temperature for 20 hours. The mixture is filtered and the solvent is stripped off in vacuo, affording

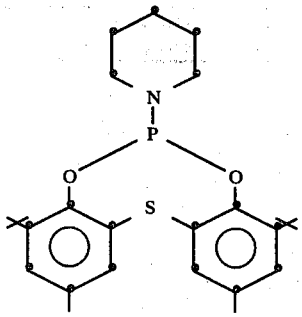

6-morpholino-2,10-dimethyl-4,8-di-tert-butyl-dibenz[d,g][1,3,6,2]dioxa-thia-phosphocine with a melting point of 200° C. (stabiliser 1).

The following stabilisers are obtained under the same reaction conditions using methylene-bis-phenols:

stabiliser 2: 6-di-n-butylamino-2,4,8,10-tetra-(1',1',3',3'-tetramethylbutyl)-12H-dibenz[d,g][1,3,2]-dioxaphosphocine (m.p. 113° C.)

stabiliser 3: 6-morpholino-2,4,8,10-tetra-(1',1',3',3'-tetramethylbutyl)-12H-dibenz[d,g][1,3,2]-dioxaphosphocine (m.p. 146° C.)

stabiliser 4: 6-morpholino-2,4,8,10-tetra-tert-butyl-12H-dibenz[d,g][1,3,2]dioxaphosphocine (m.p. 200° C.)

stabiliser 5: N,N'-dimethyl-N,N'-di-(2,4,8,10-tetra-tert-butyl-12H-dibenz[d,g][1,3,2]dioxaphosphocin-6-yl)-ethylenediamine (m.p. 260° C.)

stabiliser 6: 6-di-n-butylamino-2,4,8,10-tetra-tert-butyl-12H-dibenz[d,g][1,3,2]dioxaphosphocine (m.p. 100°-105° C.)

stabiliser 7: 6-morpholino-2,10-dimethyl-4,8-di-tert-butyl-12H-dibenz[d,g][1,3,2]dioxaphosphocine (m.p. 160° C.)

stabiliser 8: 6-(2,2,6,6-tetramethyl-piperidine-1-yl)-2,4,8,10-tetramethyl-12H-dibenz[d,g][1,3,2]dioxaphosphocine (m.p. 198° C.)

stabiliser 9: 6-di-n-butylamino-2,10-dimethyl-4,8-di-tert-butyl-12H-dibenz[d,g][1,3,2]dioxaphosphocine (m.p. 118°-120° C.)

stabiliser 10: 6-(2,2,6,6-tetramethyl-piperidine-1-yl)-2,10-dimethyl-4,8-di-tert-butyl-12H-dibenz[d,g][1,3,2]dioxaphosphocine (m.p. 188° C.).

EXAMPLE 11

100 Parts of high molecular weight polypropylene powder (Lupolen 5260 Z, available from BASF) are mixed with 0.05 part of pentaerythritol tetrakis-[3-(3,5-di-tert-butyl-4-hydroxyphenyl)propionate] and the compounds listed in Table I, and the mixture is kneaded in a Brabender plastograph at 220° C. and 50 rpm. During this time the kneading resistance is continuously recorded as torque. In the course of the kneading procedure, the polymer begins to crosslink after remaining constant for some considerable time. The crosslinking can be observed from the rapid increase in the torque. The effectiveness of the stabiliser is expressed in a prolongation of the constancy.

TABLE I

| Stabiliser | Time in minutes until change in the torque |
| --- | --- |
| 0.1 part of compound 1 | 15' |
| 0.1 part of compound 2 | 9' |
| 0.1 part of compound 3 | 9.5' |

TABLE I-continued

| Stabiliser | Time in minutes until change in the torque |
|---|---|
| 0.1 part of compound 4 | 16.5' |
| 0.05 part of compound 5 | 9' |
| 0.1 part of compound 6 | 7.0' |
| 0.1 part of compound 7 | 14.5' |
| 0.1 part of compound 8 | 14.0' |
| 0.05 part of compound 9 | 8.0' |
| 0.1 part of compound 10 | 11.5' |

EXAMPLE 12

100 Parts of polypropylene powder (Propathene HF 22, available from ICI) are mixed with 0.1 part of calcium stearate, compound 7 in the amounts indicated in Table II, and pentaerythritol tetrakis-[3-(3,5-di-tert-butyl-4-hydroxyphenyl)propionate] (0.05%).

The mixtures are extruded 5 times in succession in a single-screw extruder at a maximum temperature of 260° C. and 3 times in succession in the same extruder at 280° C., each time at 100 rpm. The melt index of the polymer is measured after the 1st, 3rd and 5th extrusion at 260° C. and after the 1st and 3rd extrusion at 280° C. The load is 2160 g, the temperature 230° C. and the measurable variable is g/10 min.

TABLE II

| Stabiliser | melt index after several extrusions | | | | |
|---|---|---|---|---|---|
| | at 260° C. | | | at 280° C. | |
| | 1. | 3. | 5. | 1. | 3. |
| without | 6.3 | 8.9 | 15.0 | 7.1 | 21.4 |
| with 0.025 part of compound 7 | 4.7 | 6.7 | 9.1 | 6.8 | 14.8 |
| with 0.05 part of compound 7 | 3.8 | 4.8 | 6.3 | 4.9 | 8.6 |

What is claimed is:

1. A compound which is 6-piperidino-2,10-dimethyl-4,8-di-tert-butyl-dibenz[d,g][1,3,6,2]dioxathiaphosphocine.